US009941478B2

(12) United States Patent
Lee et al.

(10) Patent No.: US 9,941,478 B2
(45) Date of Patent: Apr. 10, 2018

(54) ORGANIC COMPOUND, AND ORGANIC THIN FILM AND ELECTRONIC DEVICE

(71) Applicant: Samsung Electronics Co., Ltd., Suwon-si, Gyeonggi-do (KR)

(72) Inventors: Eun Kyung Lee, Seoul (KR); Jeong Il Park, Seongnam-si (KR)

(73) Assignee: SAMSUNG ELECTRONIC CO., LTD., Gyeonggi-Do (KR)

( * ) Notice: Subject to any disclaimer, the term of this patent is extended or adjusted under 35 U.S.C. 154(b) by 0 days.

(21) Appl. No.: 14/738,402

(22) Filed: Jun. 12, 2015

(65) Prior Publication Data

US 2016/0043329 A1 Feb. 11, 2016

(30) Foreign Application Priority Data

Aug. 5, 2014 (KR) ........................ 10-2014-0100632

(51) Int. Cl.
*H01L 51/00* (2006.01)
*H01L 51/05* (2006.01)
*C07D 333/50* (2006.01)

(52) U.S. Cl.
CPC ........ *H01L 51/0074* (2013.01); *C07D 333/50* (2013.01); *H01L 51/0558* (2013.01); *Y02E 10/549* (2013.01)

(58) Field of Classification Search
CPC ............ H01L 51/0074; H01L 51/0558; C07D 333/50; Y02E 10/549
See application file for complete search history.

(56) References Cited

U.S. PATENT DOCUMENTS

| | | | |
|---|---|---|---|
| 7,816,673 | B2 | 10/2010 | Park et al. |
| 8,658,805 | B2 | 2/2014 | Park et al. |
| 2009/0043113 | A1 | 2/2009 | Park et al. |
| 2013/0277657 | A1 | 10/2013 | Park et al. |
| 2013/0320316 | A1 | 12/2013 | Park et al. |

FOREIGN PATENT DOCUMENTS

| | | | | |
|---|---|---|---|---|
| JP | 2006290192 | A | | 10/2006 |
| JP | 2007197400 | A | | 8/2007 |
| JP | 2007317984 | A | | 12/2007 |
| JP | 2009120582 | A | * | 6/2009 |
| JP | 2009141338 | A | | 6/2009 |
| JP | 2010087408 | A | | 4/2010 |
| JP | 2010177641 | A | | 8/2010 |
| JP | 2010177642 | A | | 8/2010 |
| JP | 2010177644 | A | * | 8/2010 |
| JP | 2010205982 | A | | 9/2010 |
| KR | 20080054553 | A | | 6/2008 |
| KR | 20110041330 | A | * | 4/2011 |
| KR | 1020130050266 | | | 5/2013 |
| KR | 2013253080 | | | 12/2013 |
| KR | 20150016896 | A | * | 2/2015 |
| KR | 20150061811 | A | * | 6/2015 | ............. C09K 11/06 |
| KR | 20150069256 | A | * | 6/2015 | ........... C07D 403/10 |
| KR | 20150089427 | A | * | 8/2015 | ........... C07D 401/14 |
| WO | WO-9521170 | | | 8/1995 |
| WO | WO-20090009790 | A1 | | 1/2009 |
| WO | WO 2015020348 | A1 | * | 2/2015 | ........... C07D 333/76 |
| WO | WO 2015080404 | A1 | * | 6/2015 | ............. C09K 11/06 |
| WO | WO 2015088183 | A1 | * | 6/2015 | ........... C07D 403/10 |
| WO | WO 2015115756 | A1 | * | 8/2015 | ........... C07D 401/14 |

OTHER PUBLICATIONS

Proquest Machine Translation JP 2009120582 A accessed online Jun. 7, 2016, p. 1-57.*
Proquest Machine Translation KR 10-20110041330 A accessed online Jun. 7, 2016, p. 1-36.*
Proquest Machine Translation KR 10-20150016896 A accessed online Jun. 7, 2016, p. 1-39.*
Proquest Machine Translation KR 10-20150061811 A accessed online Jun. 7, 2016, p. 1-41.*
Proquest Machine Translation KR 10-20150069256 A accessed online Jun. 7, 2016, p. 1-45.*
Proquest Machine Translation KR 10-20150089427 A accessed online Jun. 7, 2016, p. 1-64.*
Proquest Machine Translation WO 2015020348 A1 accessed online Jun. 7, 2016, p. 1-43.*
Proquest Machine Translation WO 2015080404 A1 accessed online Jun. 7, 2016, p. 1-46.*
Proquest Machine Translation WO 2015088183 A1 accessed online Jun. 7, 2016, p. 1-50.*
Proquest Machine Translation WO 2015115756 A1 accessed online Jun. 7, 2016, p. 1-68.*
JP 2010177644 A; English machine translation; ProQuest Dialog; Jan. 3, 2017; p. 1-28.*
V. V. Ghaisas et al., "Thiophene Isosters of of Carcinogenic Hydrocarbons: Part III—4:10—Dimethylthionaphtheno—(6:5-b)—thionaphthene & 6:I2-Dimethyl-benzo (I:2-b, 4:5-b)-dithionaphthene", Korea Institute of Science and Technology Information, 1955, Journal of Scientific & Industrial Research, vol. 14B, pp. 11-13.
V.N. Gogte, "PMR Spectra of Some Heteroaromatic Compounds Containing Hindered Methyl Groups", National Chemical Laboratory, 1970, Indian Journal of Chemistry, vol. 9, pp. 121-124.
Munir Ahmed et al., "The Direct Brader Reaction. Part 1. Synthesis of Thiophen Analogues of Linera Polycyclic Hydrocarbons", 1973, Chemistry Department: University of Salford, pp. 1099-1102.

\* cited by examiner

*Primary Examiner* — John M Mauro
(74) *Attorney, Agent, or Firm* — Harness, Dickey & Pierce, P.L.C.

(57) ABSTRACT

An organic compound is represented by Chemical Formula 1, and an organic thin film, an organic thin film transistor, and an electronic device include the organic compound.

4 Claims, 1 Drawing Sheet

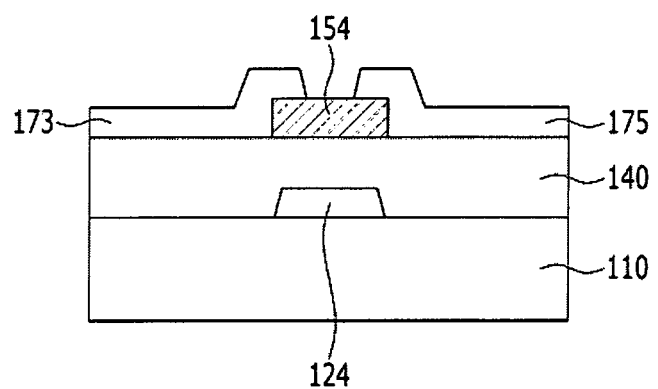

ORGANIC COMPOUND, AND ORGANIC THIN FILM AND ELECTRONIC DEVICE

CROSS-REFERENCE TO RELATED APPLICATION

This application claims priority to and the benefit of Korean Patent Application No. 10-2014-0100632 filed in the Korean Intellectual Property Office on Aug. 5, 2014, the entire contents of which are incorporated herein by reference.

BACKGROUND

1. Field

Example embodiments provide an organic compound, an organic thin film, and an electronic device.

2. Description of the Related Art

A flat panel display (e.g., a liquid crystal display (LCD), an organic light emitting diode (OLED) display, or an electrophoretic display) includes multiple pairs of field generating electrodes and an electro-optical active layer interposed therebetween.

The liquid crystal display (LCD) includes an electro-optical active layer of a liquid crystal layer, and the organic light emitting diode (OLED) display includes an electro-optical active layer of an organic emission layer.

One of paired field generating electrodes are generally connected to a switch and applied with an electrical signal, and the electro-optical active layer transforms the electrical signal to an optical signal to display an image.

The flat panel display includes a three-terminal element of a thin film transistor (TFT) as a switch. The flat panel display also includes a gate line transferring a scan signal for controlling the thin film transistor and a data line transferring a data signal to be applied to a pixel electrode.

Among the thin film transistors, an organic thin film transistor (OTFT) including an organic semiconductor (e.g., a low molecular compound or a polymer) instead of the inorganic semiconductor (e.g., silicon (Si)) has been actively researched.

The organic thin film transistor may be shaped in a fiber or a film formed according to the organic material characteristic, thereby drawing attention as a core element for a flexible display device.

The organic thin film transistor may be manufactured using a solution process (e.g., inkjet printing), and may be more easily applied to a large area flat panel display where a deposition process has a limit.

SUMMARY

Example embodiments provide an organic compound that is applicable to an electronic device, for example, an organic thin film transistor.

Example embodiments also provide an organic thin film including the organic compound.

Example embodiments also provide an electronic device including the organic thin film.

According to example embodiments, an organic compound is represented by the following Chemical Formula 1.

A-L-B    [Chemical Formula 1]

In Chemical Formula 1,

L is one of a substituted or unsubstituted $C_6$ to $C_{30}$ arylene group, a divalent substituted or unsubstituted $C_2$ to $C_{30}$ heterocyclic group, a substituted or unsubstituted $C_2$ to $C_{20}$ alkenylene group, a substituted or unsubstituted $C_2$ to $C_{20}$ alkynylene group, a substituted or unsubstituted $C_2$ to $C_{20}$ heteroalkylene group, an oxygen atom (O), a sulfur atom (S), a selenium atom (Se), a tellurium atom (Te), and a combination thereof, and each of an A moiety and a B moiety are independently a condensed polycyclic group having four or more fused rings, and are represented by one of the Chemical Formulae 2 to 4,

[Chemical Formula 2]

[Chemical Formula 3]

[Chemical Formula 4]

wherein, in Chemical Formulae 2 to 4, each of $Ar^1$ to $Ar^5$ are independently one of a substituted or unsubstituted 5-membered ring and a substituted or unsubstituted 6-membered ring, at least one of $Ar^3$ to $Ar^5$ is a substituted or unsubstituted 5-membered ring having a heteroatom, each of $Ar^1$ and $Ar^2$ forms a fused ring with an adjacent ring, each of $Ar^3$ to $Ar^5$ forms a fused ring with an adjacent ring, each of $X_1$ and $X_2$ are independently one of O, S, Se, Te, and $NR_a$, each of $R_1$ to $R_4$ and $R_a$ are independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{30}$ arylalkyl group, a substituted or unsubstituted $C_1$ to $C_{30}$ heteroalkyl group, a substituted or unsubstituted $C_2$ to $C_{30}$ heterocycloalkyl group, a substituted or unsubstituted $C_2$ to $C_{30}$ heterocyclic group, a substituted or unsubstituted $C_2$ to $C_{30}$ alkenyl group, a substituted or unsubstituted $C_2$ to $C_{30}$ alkynyl group, a hydroxy group, a halogen atom, and a combination thereof, each of a to f are independently integers ranging from 1 to 3, and

* indicates a linking point.

Each of the $Ar^1$ to $Ar^5$ may independently be one of a substituted or unsubstituted benzene ring and a substituted or unsubstituted heterocyclic group.

The at least one of the $Ar^1$ and $Ar^2$ may be a heterocyclic group including one of O, S, Se, Te, and $NR_a$, and at least one of the $Ar^3$ to $Ar^5$ may be a heterocyclic group including one of O, S, Se, Te, and $NR_a$, wherein $R_a$ is one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{30}$ arylalkyl group, a substituted or unsubstituted $C_1$ to $C_{30}$ heteroalkyl group, a substituted or unsubstituted $C_2$ to $C_{30}$ heterocycloalkyl group, a substituted or unsubstituted $C_2$ to $C_{30}$ heterocyclic group, a substituted or unsubstituted $C_2$ to $C_{30}$ alkenyl group, a substituted or unsubstituted $C_2$ to $C_{30}$ alkynyl group, a hydroxy group, a halogen atom, and a combination thereof.

The $Ar^1$ and $Ar^2$ of Chemical Formula 2 or 3 may be different, and one of $Ar^3$ to $Ar^5$ of Chemical Formula 4 may be different from the others.

One of the $Ar^1$ and $Ar^2$ of Chemical Formula 2 or 3 may be a substituted or unsubstituted benzene ring, and the other of the $Ar^1$ and $Ar^2$ may be a substituted or unsubstituted heterocyclic group.

The $Ar^3$ and $Ar^4$ of Chemical Formula 4 may be a substituted or unsubstituted heterocyclic group and the $Ar^5$ may be a substituted or unsubstituted benzene ring.

The $Ar^4$ and $Ar^5$ of Chemical Formula 4 may be a substituted or unsubstituted heterocyclic group and the $Ar^3$ may be a substituted or unsubstituted benzene ring.

The $Ar^3$ and $Ar^5$ of Chemical Formula 4 may be a substituted or unsubstituted heterocyclic group and the $Ar^4$ may be a substituted or unsubstituted benzene ring.

Each of the A moiety and the B moiety may independently be one of the groups listed in the Group 1.

[Group 1]

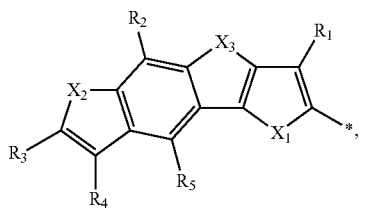

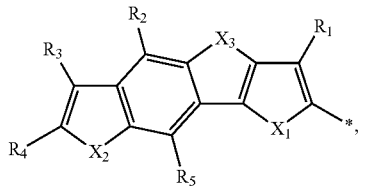

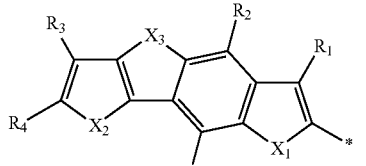

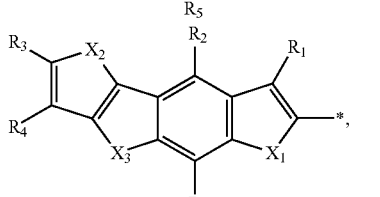

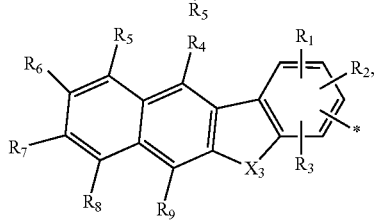

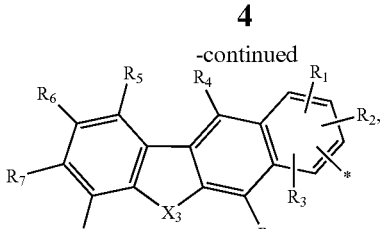

-continued

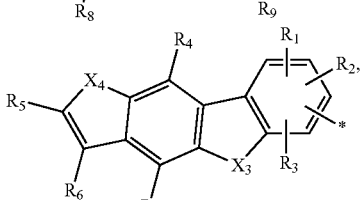

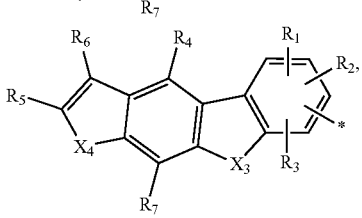

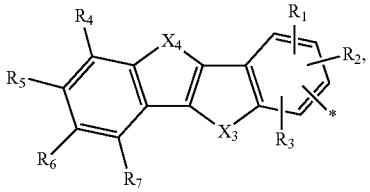

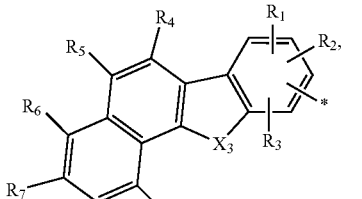

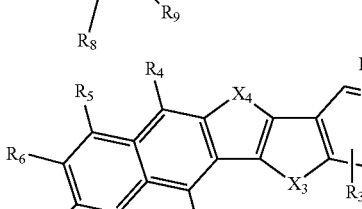

In Group 1,
each of $X_1$ to $X_4$ are independently one of O, S, Se, Te, and $NR_a$,
each of $R_1$ to $R_9$ and $R_a$ are independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{30}$ arylalkyl group, a substituted or unsubstituted $C_1$ to $C_{30}$ heteroalkyl group, a substituted orunsubstituted $C_2$ to $C_{30}$ heterocycloalkyl group, a substituted or unsubstituted $C_2$ to $C_{30}$ heterocyclic group, a substituted or unsubstituted $C_2$ to $C_{30}$ alkenyl group, a substituted or unsubstituted $C_2$ to $C_{30}$ alkynyl group, a hydroxy group, a halogen atom, and a combination thereof, and
* indicates a linking point.

The organic compound may be represented by one of the Chemical Formulae 5 to 37.

[Chemical Formula 5]
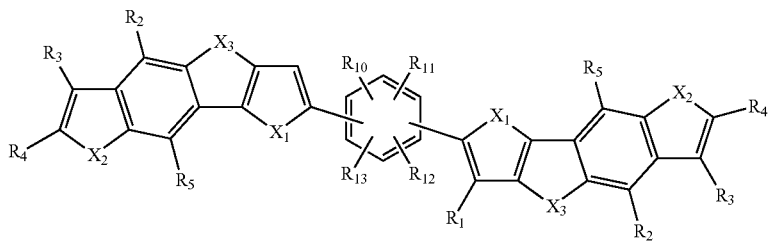
[Chemical Formula 6]
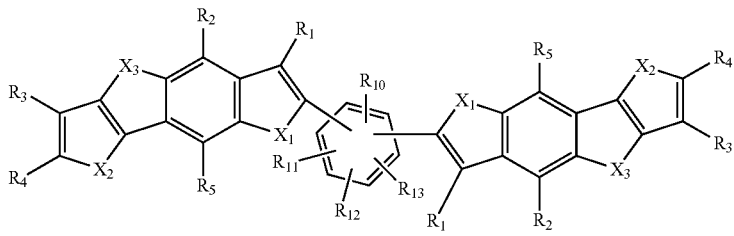
[Chemical Formula 7]
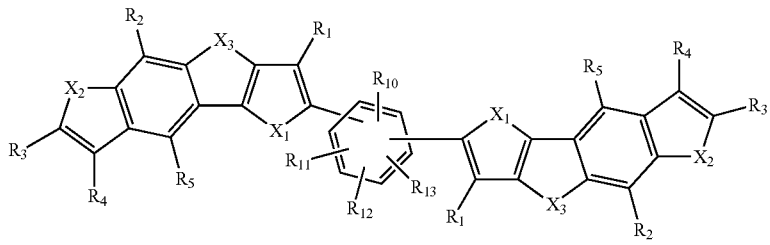
[Chemical Formula 8]
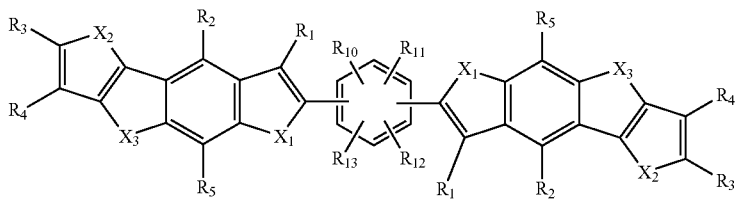
[Chemical Formula 9]
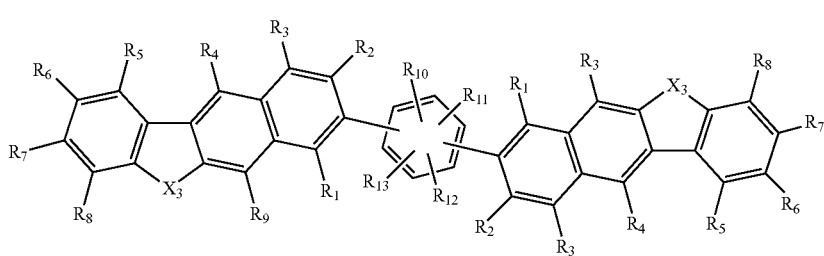
[Chemical Formula 10]
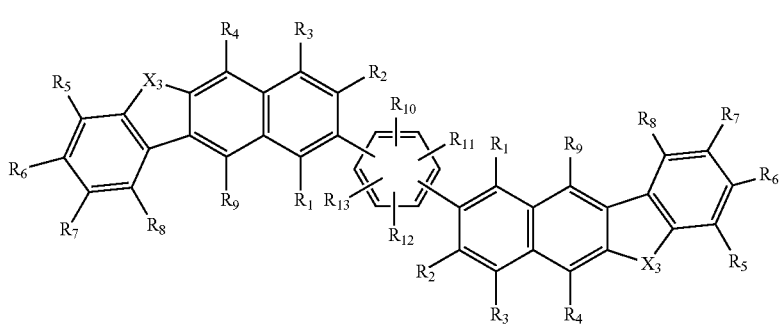

[Chemical Formula 11]
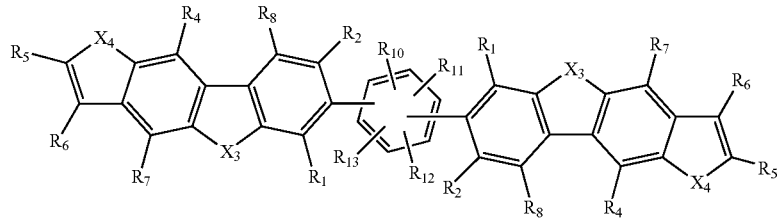
[Chemical Formula 12]
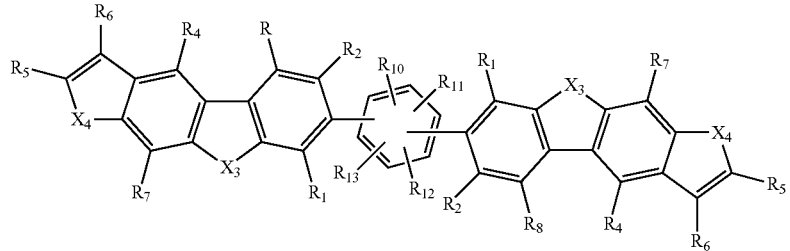
[Chemical Formula 13]
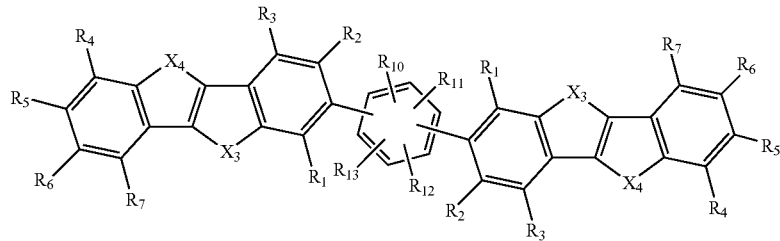
[Chemical Formula 14]
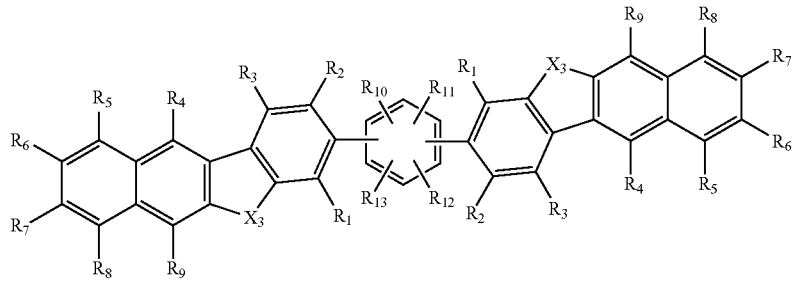
[Chemical Formula 15]
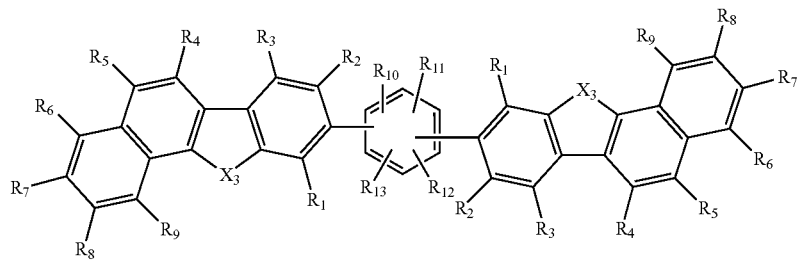
[Chemical Formula 16]
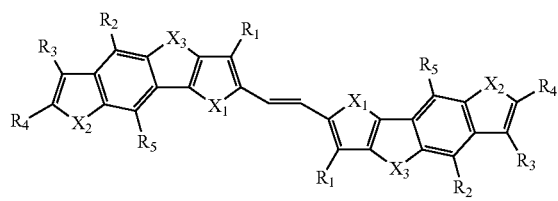
[Chemical Formula 17]
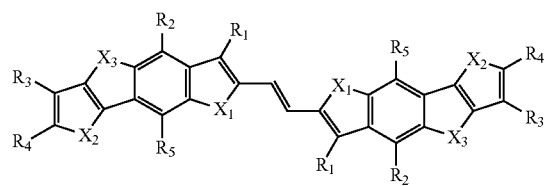

[Chemical Formula 18]
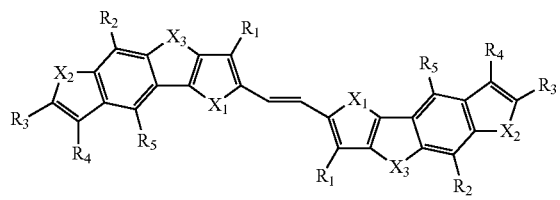
[Chemical Formula 19]
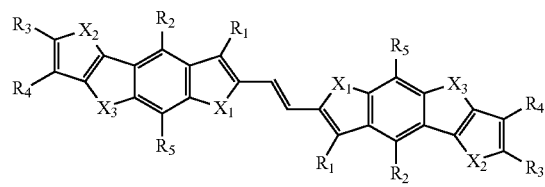
[Chemical Formula 20]
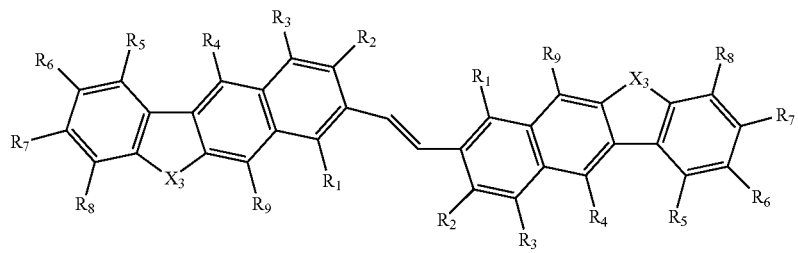
[Chemical Formula 21]
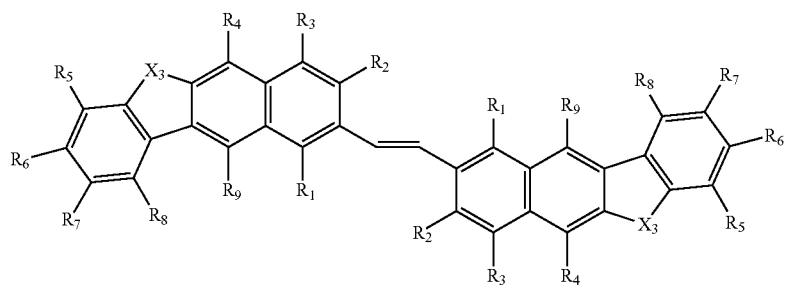
[Chemical Formula 22]
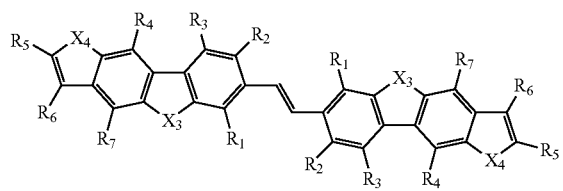
[Chemical Formula 23]
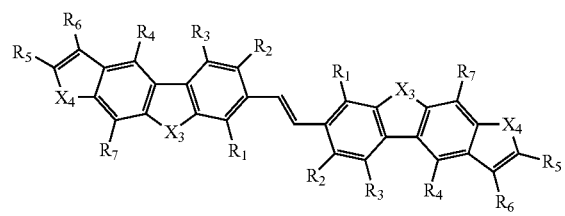
[Chemical Formula 24]
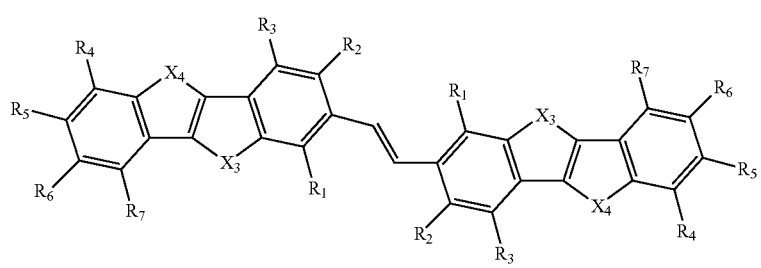
[Chemical Formula 25]
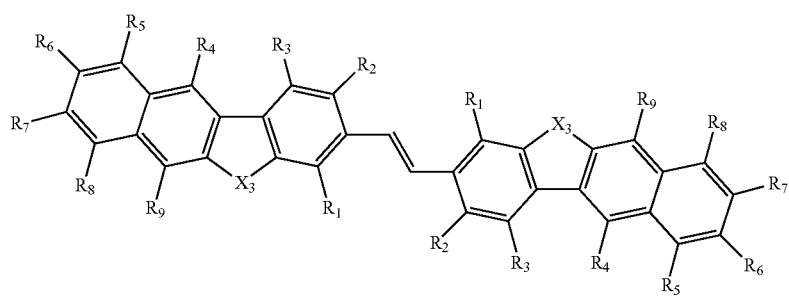

-continued
[Chemical Formula 26]
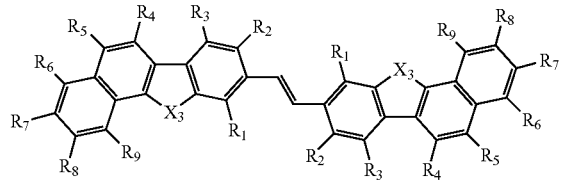
[Chemical Formula 27]
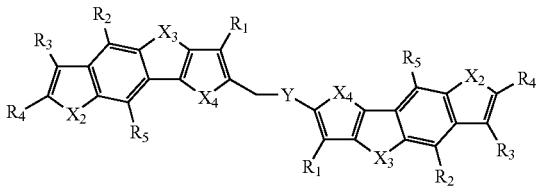
[Chemical Formula 28]
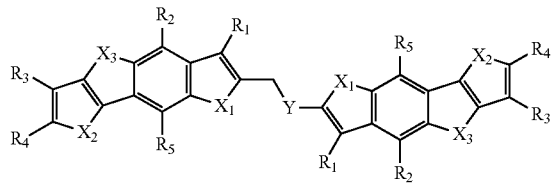
[Chemical Formula 29]
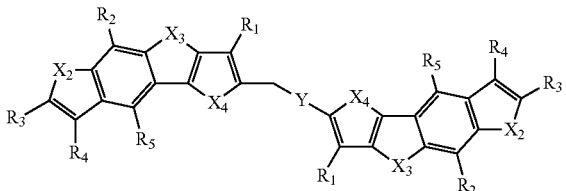
[Chemical Formula 30]
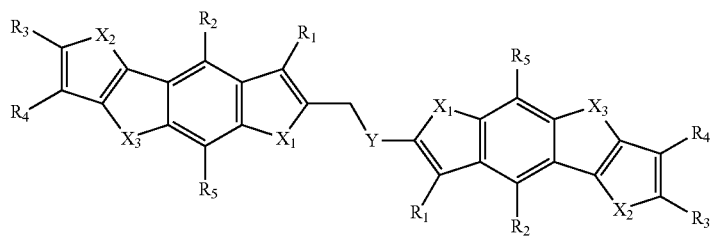
[Chemical Formula 31]
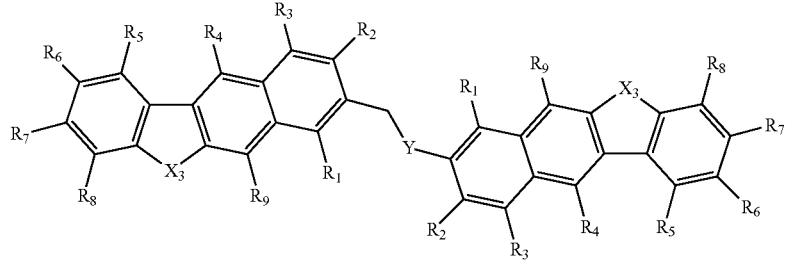
[Chemical Formula 32]
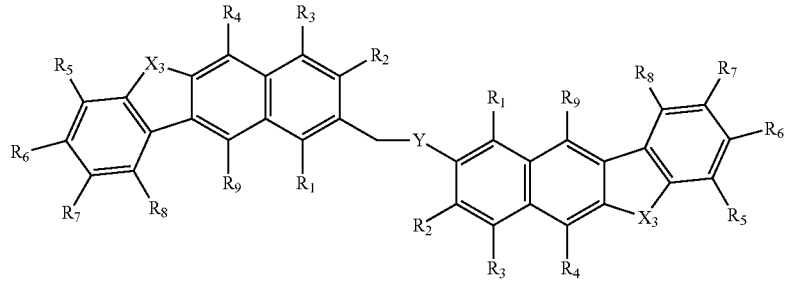
[Chemical Formula 33]
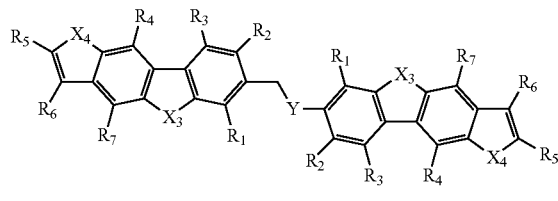
[Chemical Formula 34]
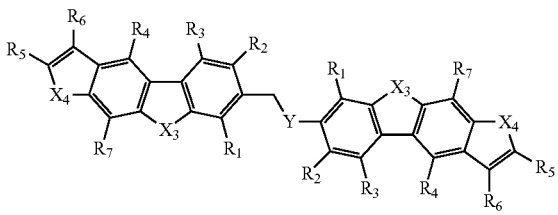

[Chemical Formula 35]

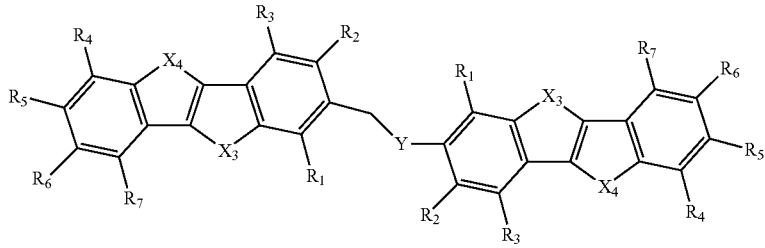

[Chemical Formula 36]

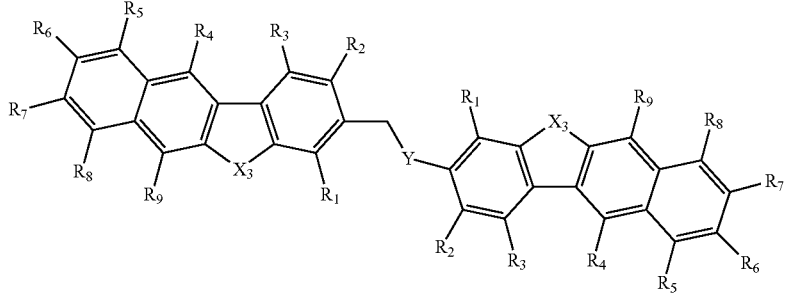

[Chemical Formula 37]

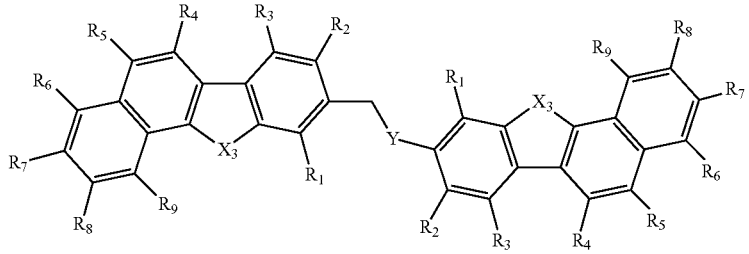

In Chemical Formulae 5 to 37, each of $X_1$ to $X_4$ are independently one of O, S, Se, Te, and $NR_a$, Y is one of O, S, Se, and Te, and each of $R_1$ to $R_{13}$ and $R_a$ are independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{30}$ arylalkyl group, a substituted or unsubstituted $C_1$ to $C_{30}$ heteroalkyl group, a substituted or unsubstituted $C_2$ to $C_{30}$ heterocycloalkyl group, a substituted or unsubstituted $C_2$ to $C_{30}$ heterocyclic group, a substituted or unsubstituted $C_2$ to $C_{30}$ alkenyl group, a substituted or unsubstituted $C_2$ to $C_{30}$ alkynyl group, a hydroxy group, a halogen atom, and a combination thereof.

Each of the $R_{10}$ to $R_{13}$ may independently be one of hydrogen and a halogen atom.

According to example embodiments, an organic thin film includes the organic compound.

According to example embodiments, an electronic device includes the organic thin film.

According to example embodiments, an organic thin film transistor includes a gate electrode, an organic semiconductor overlapping the gate electrode, and a source electrode and a drain electrode electrically connected to the organic semiconductor, wherein the organic semiconductor includes an organic compound represented by the Chemical Formula 1.

According to example embodiments, an electronic device includes the organic thin film transistor.

The electronic device may include a solar cell, a liquid crystal display (LCD), an organic light emitting diode (OLED) display, an electrophoretic display device, an organic photoelectric device, and an organic sensor.

According to example embodiments, an electronic device includes the organic thin film.

BRIEF DESCRIPTION OF THE DRAWING

A cross-sectional view of an organic thin film transistor according to example embodiments is shown.

DETAILED DESCRIPTION

Example embodiments will hereinafter be described in detail, and may be more easily performed by those who have common knowledge in the related art. However, this disclosure may be embodied in many different forms and is not to be construed as limited to the example embodiments set forth herein.

In the drawing, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawing, parts having no relationship with the description are omitted for clarity of the embodiments, and the same or similar constituent elements are indicated by the same reference numerals throughout the specification.

It will be understood that when an element or layer is referred to as being "on," "connected to," "coupled to," or "covering" another element or layer, it may be directly on, connected to, coupled to, or covering the other element or layer, or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It will be understood that, although the terms first, second, third, etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the example embodiments.

Spatially relative terms, e.g., "beneath," "below," "lower," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of the example embodiments. As used herein, the singular forms "a," "an," and "the" are intended to include the plural forms as well, unless the context clearly indicates otherwise. It will be further understood that the terms "comprises," "comprising," "includes," and/or "including," if used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art. It will be further understood that terms, including those defined in commonly used dictionaries, should be interpreted as having a meaning that is consistent with their meaning in the context of the relevant art and will not be interpreted in an idealized or overly formal sense unless expressly so defined herein.

As used herein, when a definition is not otherwise provided, the term "substituted" refers to one substituted with a substituent selected from a halogen atom (F, Br, Cl, or I), a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, phosphoric acid or a salt thereof, a $C_1$ to $C_{20}$ alkyl group, a $C_2$ to $C_{20}$ alkenyl group, a $C_2$ to $C_{20}$ alkynyl group, a $C_6$ to $C_{30}$ aryl group, a $C_7$ to $C_{30}$ arylalkyl group, a $C_1$ to $C_{30}$ alkoxy group, a $C_1$ to $C_{20}$ heteroalkyl group, a $C_3$ to $C_{20}$ heteroarylalkyl group, a $C_3$ to $C_{30}$ cycloalkyl group, a $C_3$ to $C_{15}$ cycloalkenyl group, a $C_6$ to $C_{15}$ cycloalkynyl group, a $C_3$ to $C_{30}$ heterocycloalkyl group, and a combination thereof, instead of hydrogen of a compound.

As used herein, when a definition is not otherwise provided, the term "hetero" refers to one including 1 to 3 heteroatoms selected from N, O, S, Se, and P.

Hereinafter, an organic compound according to example embodiments is described.

An organic compound according to example embodiments is represented by the Chemical Formula 1.

A-L-B [Chemical Formula 1]

In Chemical Formula 1,

L is one of a substituted or unsubstituted $C_6$ to $C_{30}$ arylene group, a divalent substituted or unsubstituted $C_2$ to $C_{30}$ heterocyclic group, a substituted or unsubstituted $C_2$ to $C_{20}$ alkenylene group, a substituted or unsubstituted $C_2$ to $C_{20}$ alkynylene group, a substituted or unsubstituted $C_2$ to $C_{20}$ heteroalkylene group, an oxygen atom (O), a sulfur atom (S), a selenium atom (Se), a tellurium atom (Te), and a combination thereof, and each of an A moiety and a B moiety are independently a condensed polycyclic group including four or more fused rings, and are represented by one of the Chemical Formulae 2 to 4.

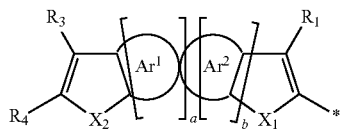

[Chemical Formula 2]

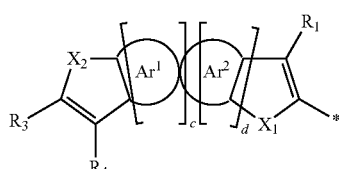

[Chemical Formula 3]

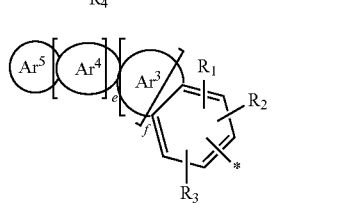

[Chemical Formula 4]

In Chemical Formulae 2 to 4, each of $Ar^1$ to $Ar^5$ are independently one of a substituted or unsubstituted 5-membered ring and a substituted or unsubstituted 6-membered ring, at least one of $Ar^3$ to $Ar^5$ is a substituted or unsubstituted 5-membered ring having a heteroatom, each of $Ar^1$ and $Ar^2$ forms a fused ring with an adjacent ring, each of $Ar^3$ to $Ar^5$ forms a fused ring with an adjacent ring, each of $X_1$ and $X_2$ are independently one of O, S, Se, Te and $NR_a$, each of $R_1$ to $R_4$ and $R_a$ are independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{30}$ arylalkyl group, a substituted or unsubstituted $C_1$ to $C_{30}$ heteroalkyl group, a substituted or unsubstituted $C_2$ to $C_{30}$ heterocycloalkyl group, a substituted or unsubstituted $C_2$ to $C_{30}$ heterocyclic group, a substituted or unsubstituted $C_2$ to $C_{30}$ alkenyl group, a substituted or unsubstituted $C_2$ to $C_{30}$ alkynyl group, a hydroxy group, a halogen atom, and a combination thereof, each of a to f are independently integers ranging from 1 to 3, and

* indicates a linking point.

The organic compound is a low molecular compound where an A moiety of a condensed polycyclic group including four or more fused rings and a B moiety of a condensed polycyclic group including four or more fused rings are linked to each other through a linking group (L).

The organic compounds may increase charge mobility by appropriately adjusting the number of rings in the polycyclic groups and thereby increasing planarization properties of the organic compound and packing and stacking properties among the compounds. The organic compound may increase charge mobility by linking the two condensed polycyclic groups through an arylene group, a divalent multiple bonding group, and/or a divalent heteroatom-containing group and thereby increasing an orbital overlap among compounds.

Herein, the A moiety and the B moiety may not be positioned on the same plane but may be twisted with a predetermined or given angle.

An organic compound having a structure in which the A moiety and the B moiety are linked to an arylene group, a divalent multiple bonding group, and/or a divalent heteroatom-containing group may be easily synthesized and highly dissolved as well as maintain an overlap among compounds, compared with a compound having a structure in which the A moiety and the B moiety are fused to each other. Accordingly, a yield of the organic compound may be increased and may be easily applied to a solution process during formation of an organic thin film. As a result, the organic compound may increase processability of an electronic device as well as improve its electrical characteristics.

Each of the A moiety and the B moiety is a fused ring of a substituted or unsubstituted benzene ring and a substituted or unsubstituted heterocyclic group.

At least one of the $Ar^1$ and $Ar^2$ of Chemical Formula 2 or 3 may be a heterocyclic group including one of O, S, Se, Te and $NR_a$, and at least one of $Ar^3$ to $Ar^5$ of Chemical Formula 4 may be a heterocyclic group including one of O, S, Se, Te and $NR_a$. Herein, $R_a$ may be one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{30}$ arylalkyl group, a substituted or unsubstituted $C_1$ to $C_{30}$ heteroalkyl group, a substituted or unsubstituted $C_2$ to $C_{30}$ heterocycloalkyl group, a substituted or unsubstituted $C_2$ to $C_{30}$ heterocyclic group, a substituted or unsubstituted $C_2$ to $C_{30}$ alkenyl group, a substituted or unsubstituted $C_2$ to $C_{30}$ alkynyl group, a hydroxy group, a halogen atom, and a combination thereof.

For example, the $Ar^1$ and $Ar^2$ of Chemical Formula 2 or 3 may be different, and for example at least one of $Ar^1$ and $Ar^2$ may be a substituted or unsubstituted benzene ring, and the other one may be a substituted or unsubstituted heterocyclic group.

For example, one of $Ar^3$ to $Ar^5$ of Chemical Formula 4 may be different from the others. For example, $Ar^3$ and $Ar^4$ may be the same and may be different from $Ar^5$, wherein $Ar^3$ and $Ar^4$ may be a substituted or unsubstituted heterocyclic group, and $Ar^5$ may be a substituted or unsubstituted benzene ring. For example, $Ar^4$ and $Ar^5$ may be the same and may be different from $Ar^3$, wherein $Ar^4$ and $Ar^5$ may be a substituted or unsubstituted benzene ring, and $A^3$ may be a substituted or unsubstituted heterocyclic group. For example, $Ar^3$ and $Ar^5$ may be the same and may be different from $Ar^4$, wherein $Ar^3$ and $Ar^5$ may be a substituted or unsubstituted benzene ring, and $Ar^4$ may be a substituted or unsubstituted heterocyclic group, or $Ar^3$ and $Ar^5$ may be a substituted or unsubstituted heterocyclic group, and $Ar_4$ may be a substituted or unsubstituted benzene ring.

For example, L of Chemical Formula 1 may be one of a substituted or unsubstituted $C_6$ to $C_{30}$ arylene group, a divalent substituted or unsubstituted $C_2$ to $C_{30}$ heterocyclic group, a substituted or unsubstituted $C_2$ to $C_{20}$ alkenylene group, a substituted or unsubstituted $C_2$ to $C_{20}$ heteroalkylene group, and a combination thereof. The substituted $C_6$ to $C_{30}$ arylene group may be, for example, substituted with one of an alkyl group, a halogen atom, and a combination thereof. The halogen atom may be, for example, fluorine.

The A moiety and the B moiety may be the same or different.

Each of the A moiety and the B moiety may independently be, for example, one of the groups listed in the Group 1, but are not limited thereto.

[Group 1]

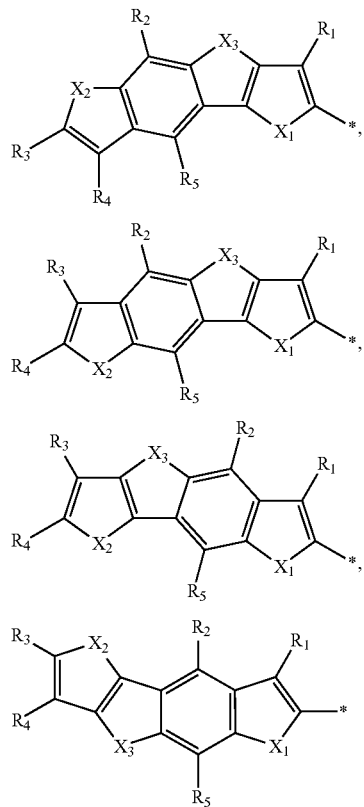

-continued

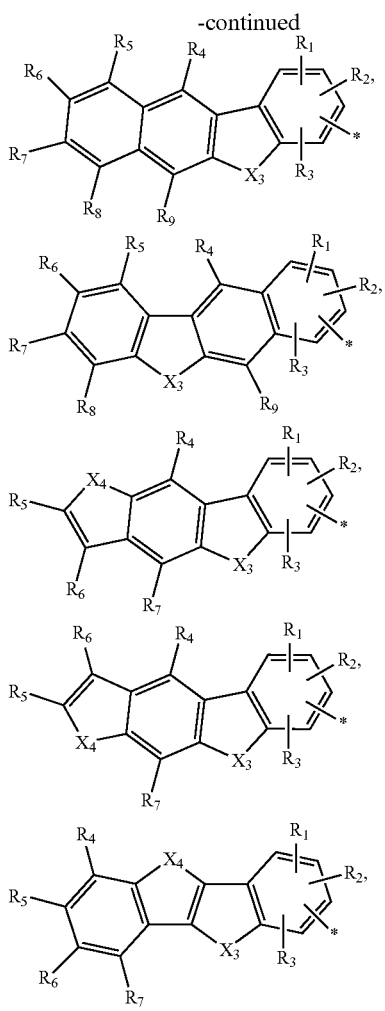

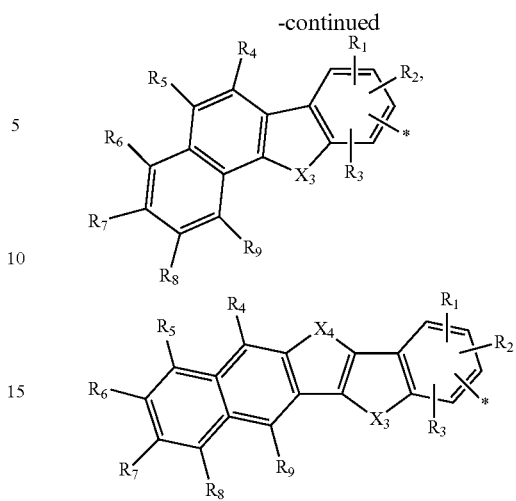

In Group 1,
each of $X_1$ to $X_4$ are independently one of O, S, Se, Te and $NR_a$,
each of $R_1$ to $R_9$ and $R_a$ are independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{30}$ arylalkyl group, a substituted or unsubstituted $C_1$ to $C_{30}$ heteroalkyl group, a substituted or unsubstituted $C_2$ to $C_{30}$ heterocycloalkyl group, a substituted or unsubstituted $C_2$ to $C_{30}$ heterocyclic group, a substituted or unsubstituted $C_2$ to $C_{30}$ alkenyl group, a substituted or unsubstituted $C_2$ to $C_{30}$ alkynyl group, a hydroxy group, a halogen atom, and a combination thereof, and
* indicates a linking point.

The organic compound may be, for example, represented by one of the Chemical Formulae 5 to 37, but is not limited thereto.

[Chemical Formula 5]

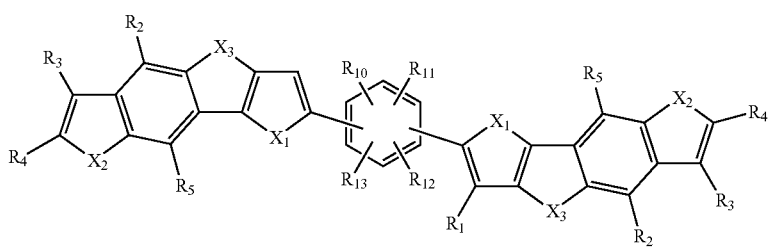

[Chemical Formula 6]

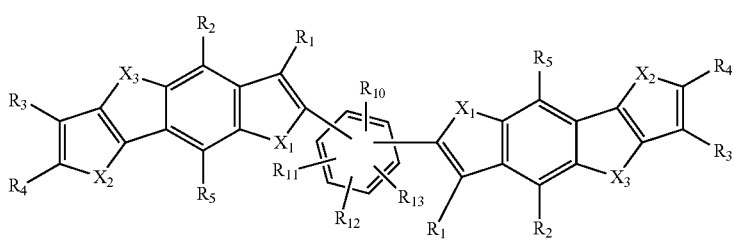

[Chemical Formula 7]
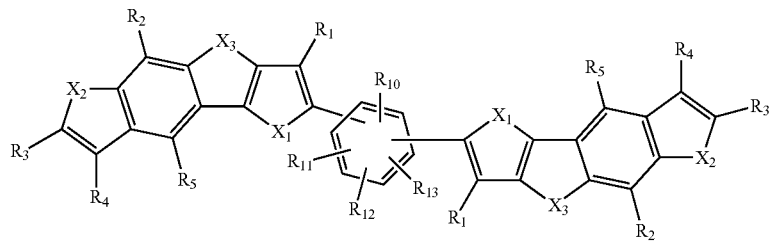
[Chemical Formula 8]
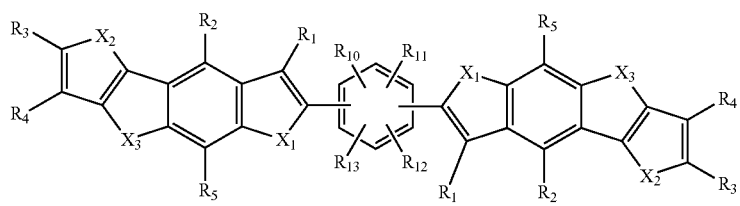
[Chemical Formula 9]
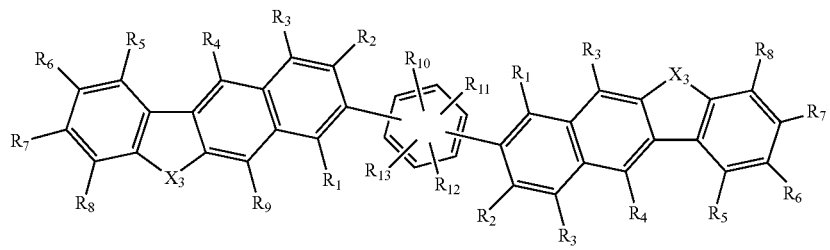
[Chemical Formula 10]
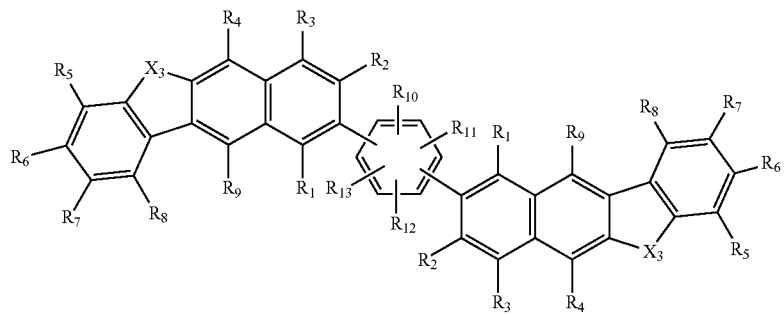
[Chemical Formula 11]
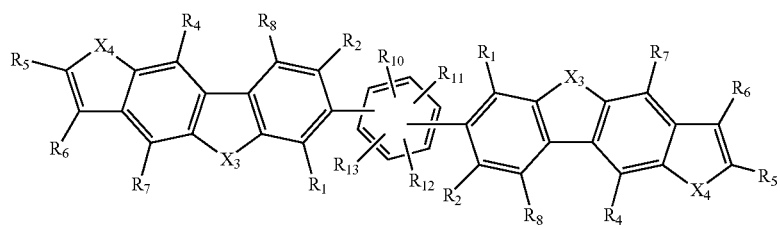
[Chemical Formula 12]
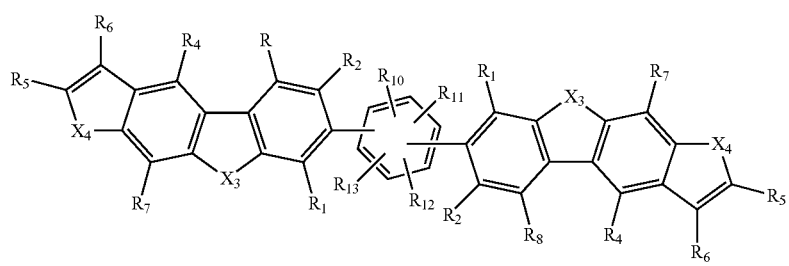

[Chemical Formula 13]
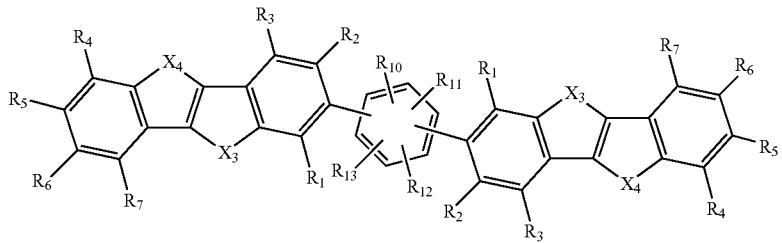
[Chemical Formula 14]
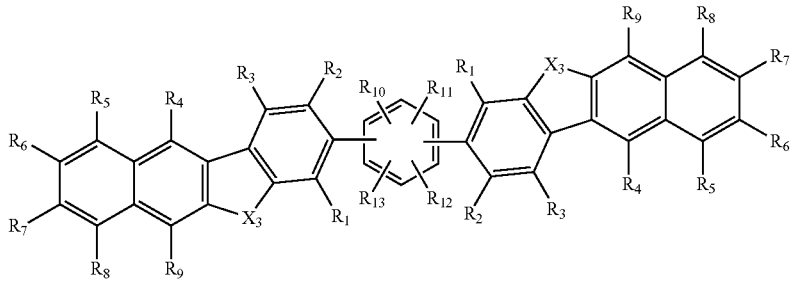
[Chemical Formula 15]
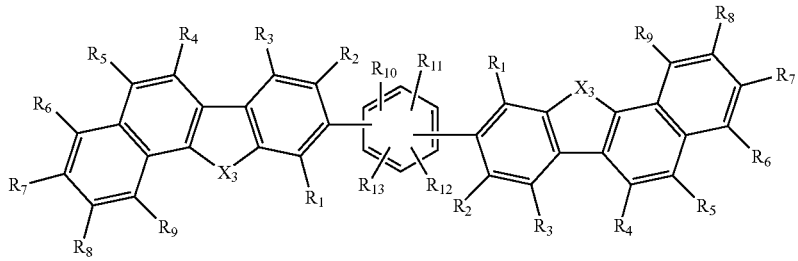
[Chemical Formula 16]
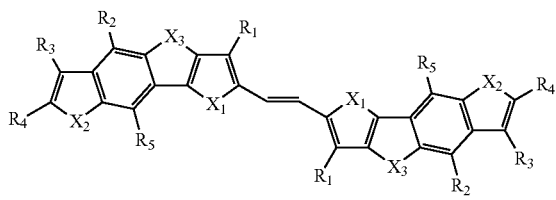
[Chemical Formula 17]
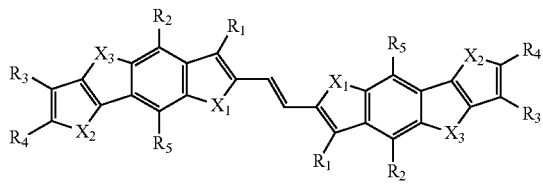
[Chemical Formula 18]
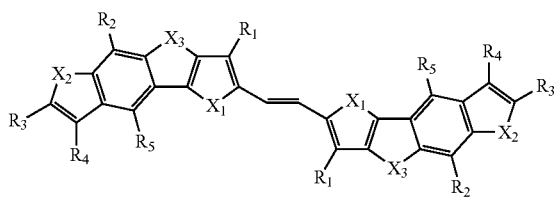
[Chemical Formula 19]
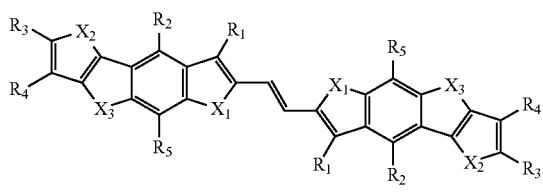
[Chemical Formula 20]
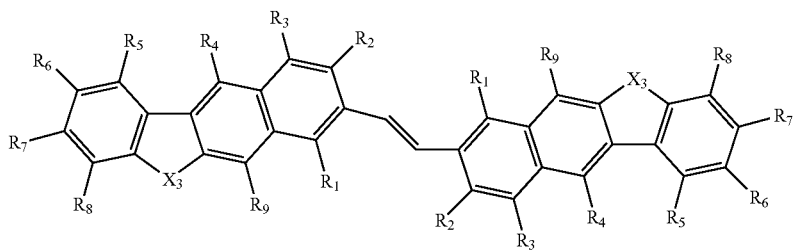

-continued
[Chemical Formula 21]
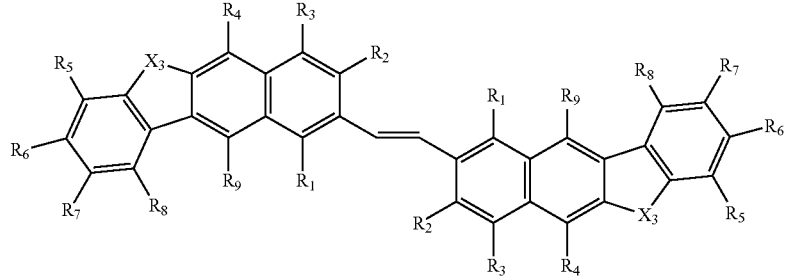
[Chemical Formula 22]
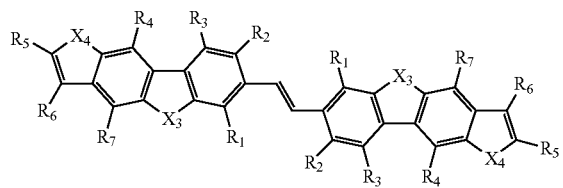
[Chemical Formula 23]
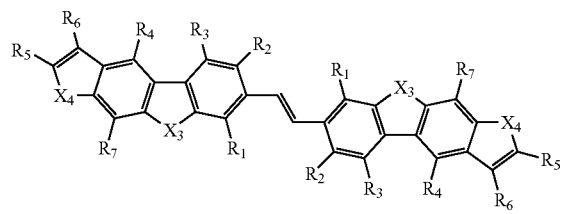
[Chemical Formula 24]
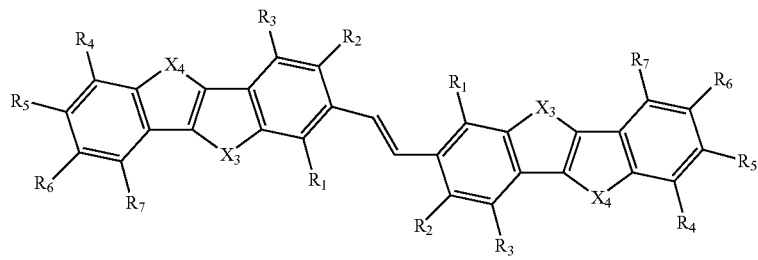
[Chemical Formula 25]
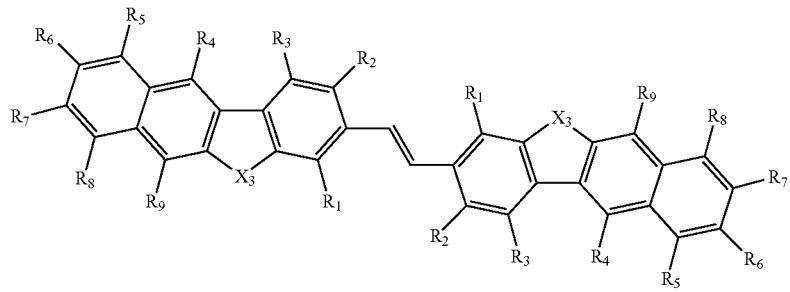
[Chemical Formula 26]
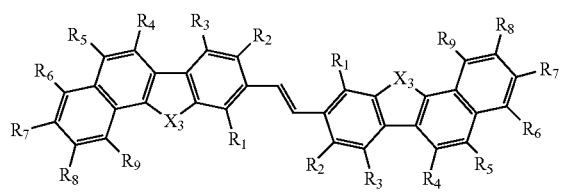
[Chemical Formula 27]
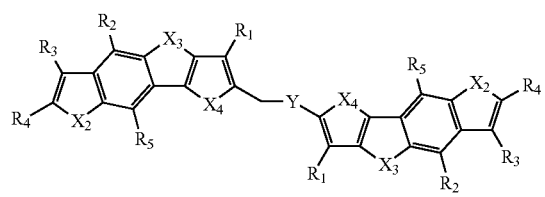
[Chemical Formula 28]
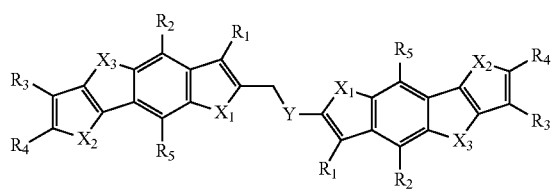
[Chemical Formula 29]
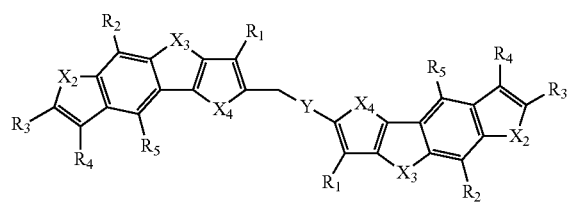

-continued
[Chemical Formula 30]
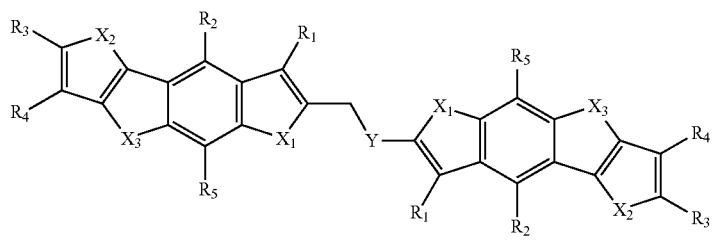
[Chemical Formula 31]
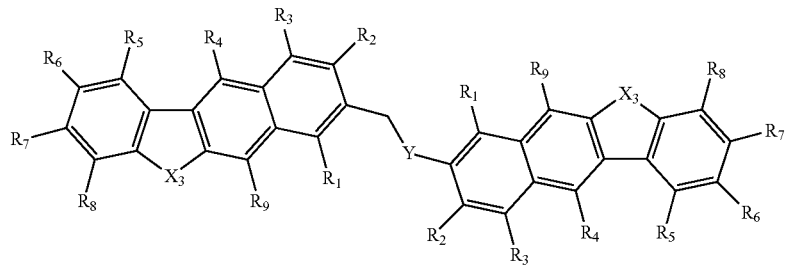
[Chemical Formula 32]
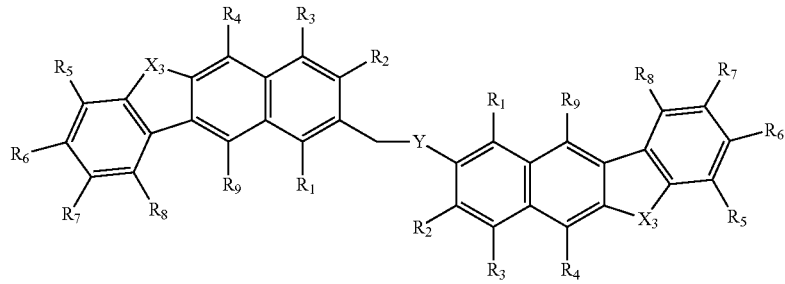
[Chemical Formula 33]
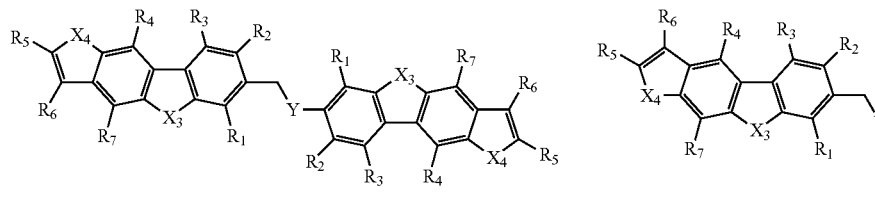
[Chemical Formula 34]
[Chemical Formula 35]
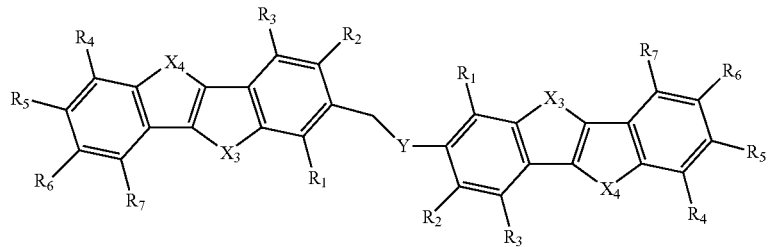
[Chemical Formula 36]
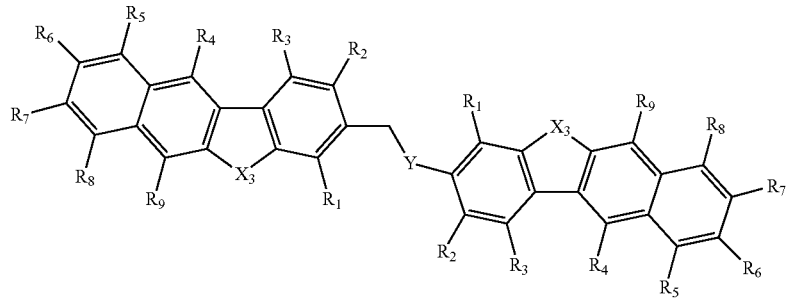

[Chemical Formula 37]

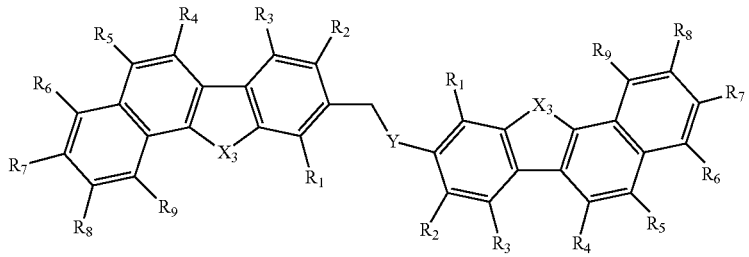

In Chemical Formulae 5 to 37, each of $X_1$ to $X_4$ are independently one of O, S, Se, Te and $NR_a$, Y is one of O, S, Se and Te, and each of $R_1$ to $R_{13}$ and $R_a$ are independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{30}$ arylalkyl group, a substituted or unsubstituted $C_1$ to $C_{30}$ heteroalkyl group, a substituted or unsubstituted $C_2$ to $C_{30}$ heterocycloalkyl group, a substituted or unsubstituted $C_2$ to $C_{30}$ heterocyclic group, a substituted or unsubstituted $C_2$ to $C_{30}$ alkenyl group, a substituted or unsubstituted $C_2$ to $C_{30}$ alkynyl group, a hydroxy group, a halogen atom and a combination thereof.

For example, each of $R_{10}$ to $R_{13}$ of Chemical Formulae 5 to 15 may independently be one of hydrogen and a halogen atom. For example, $R_{10}$ to $R_{13}$ of Chemical Formulae 5 to 15 may all be hydrogen, or may include one to four halogen atoms. The halogen atom may be, for example, fluorine.

For example, each of $X_1$ to $X_4$ of Chemical Formulae 5 to 37 may independently be sulfur (S).

For example, Y of Chemical Formulae 27 to 37 may be oxygen (O) or sulfur (S).

For example, each of $R_1$ to $R_9$ of Chemical Formulae 5 to 37 may independently be hydrogen.

The organic compound may be formed into an organic thin film by a deposition or solution process. The organic thin film may be applied to various devices including an organic semiconductor. For example, the organic compound may be applied to an organic thin film transistor, and may be applied to a charge transport layer and/or an active layer of an electronic device (e.g., a solar cell, a liquid crystal display (LCD), an organic light emitting diode (OLED) display, an electrophoretic display, an organic photoelectric device, and an organic sensor).

Hereinafter, one example of an organic thin film transistor including the organic compound is described referring to the drawing.

In the drawing, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

A cross-sectional view of an organic thin film transistor according to example embodiments is shown.

A gate electrode 124 is formed on a substrate 110 made of transparent glass, silicon, or plastic. The gate electrode 124 is connected to a gate line (not shown) transferring a gate signal. The gate electrode 124 may be made of one of gold (Au), copper (Cu), nickel (Ni), aluminum (Al), molybdenum (Mo), chromium (Cr), tantalum (Ta), titanium (Ti), an alloy thereof, and a combination thereof.

A gate insulating layer 140 is formed on the gate electrode 124. The gate insulating layer 140 may be made of an organic material or an inorganic material. Examples of the organic material may include a soluble polymer compound, for example, a polyvinyl alcohol-based compound, a polyimide-based compound, a polyacryl-based compound, a polystyrene-based compound, and benzocyclobutane (BCB), and examples of the inorganic material may include a silicon nitride ($SiN_x$) and a silicon oxide ($SiO_x$).

A source electrode 173 and a drain electrode 175 are formed on the gate insulating layer 140. The source electrode 173 and the drain electrode 175 face each other with the gate electrode 124 therebetween. The source electrode 173 is electrically connected to the data line (not shown) transferring the data signal. The source electrode 173 and the drain electrode 175 may include at least one metal selected from gold (Au), copper (Cu), nickel (Ni), aluminum (Al), molybdenum (Mo), chromium (Cr), tantalum (Ta), titanium (Ti), an alloy thereof, or a combination thereof.

An organic semiconductor 154 is formed on the source electrode 173 and the drain electrode 175. The organic semiconductor 154 may be made of the organic compound. The organic semiconductor 154 may be formed in a solution process (e.g., spin coating, slit coating, or inkjet printing) by preparing the above organic semiconductor as a solution. However, the organic compound may be formed using a dry process (e.g., deposition).

Although the bottom gate structured organic thin film transistor is illustrated as an organic thin film transistor, it is not limited thereto, and it may be applied to all organic thin film transistors (e.g., a top gate structured organic thin film transistor).

The organic thin film transistor may be applied to a switch or driving device of various electronic devices, and the electronic device may be, for example, a liquid crystal display (LCD), an organic light emitting diode (OLED) display, an electrophoretic display device, or an organic sensor.

Hereinafter, the present disclosure is illustrated in more detail with reference to examples. However, these are examples, and the present disclosure is not limited thereto.

Synthesis of Organic Compound

Synthesis Example 1

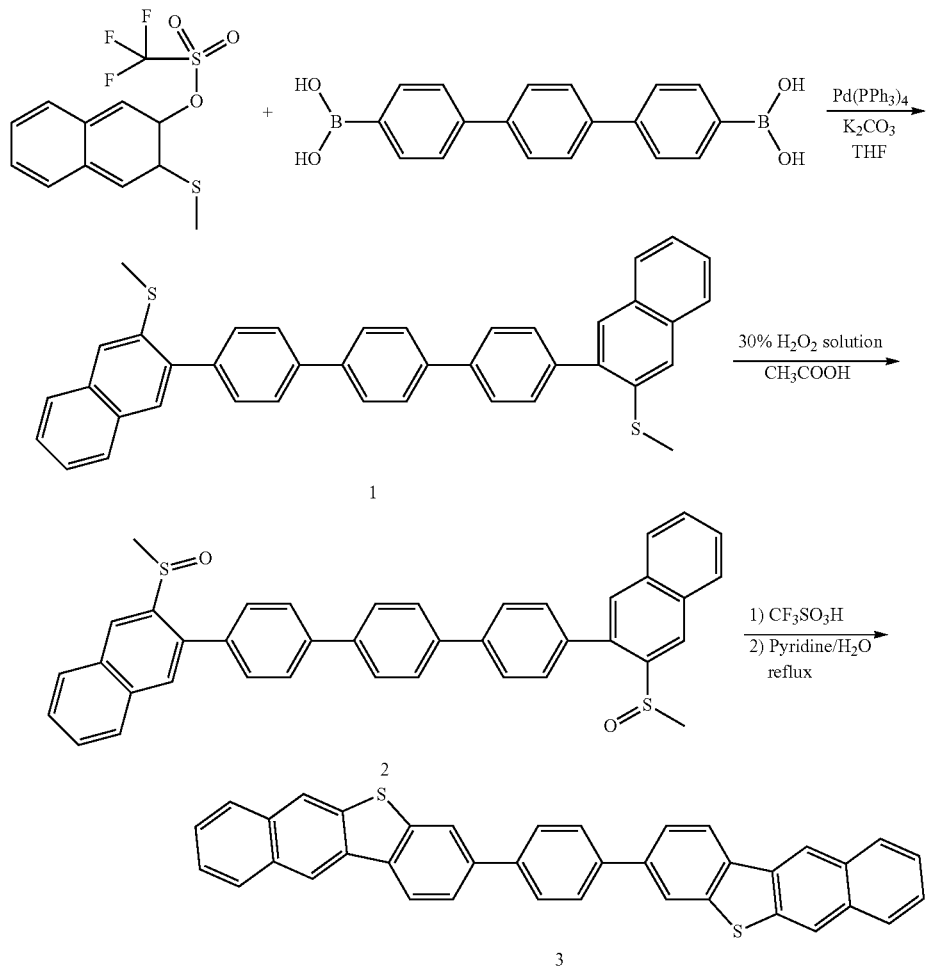

1. Synthesis of Compound 1

7.94 g (0.057 mol) of K$_2$CO$_3$ is put in a 3-necked flask under a nitrogen atmosphere, and then 60 ml of distilled water and 100 ml of THF are subsequently added thereto. Then, 6.66 g (0.02 mol) of 3-(methylthio)-2,3-dihydronaphthalen-2-yl trifluoromethane sulfonate and 2.61 g (0.008 mol) of [1,1':4',1''-terphenyl]-4,4''-diyldiboronic acid are added to the solution, 1.42 g (0.00123 mol) of tetrakis(triphenylphosphine) palladium (0) is added thereto, and the resulting mixture is refluxed. Five hours later, a 1N HCl solution is added thereto to complete the reaction, and the reactant is extracted with ethyl acetate. The resultant is dried with MgSO$_4$, and a solvent is removed, obtaining the compound 1. The obtained solid is washed several times with ether, obtaining 2 g of a yellow solid. The yield is 57%.

1H NMR (500 MHz, CDCl3): g of a d w-7.73 (m, 7H), 7.61 (m, 3H), 7.49 (t, 1H), 7.46 (t, 1H), 2.53 (s, 3H)

2. Synthesis of Compound 2

2 g (0.00348 mol) of the compound 1 is suspended in 200 ml of acetic acid, and then 0.83 g (0.0073 mol) of a 30% H$_2$O$_2$ solution is slowly added thereto. Subsequently, the mixture is heated at 40° C. and agitated for 48 hours, and then acetic acid is removed, obtaining 1 g of a yellow solid compound 2.

1H NMR (500 MHz, CDCl3): en acetic (s, 1H), 8.06 (d, 1H), 7.95 (d, 1H), 7.86 (s, 1H), 7.81 (m, 4H), 7.63 (m, 4H), 2.44 (s, 3H)

3. Synthesis of 2,2'-binaphtho[2,3-b]thieno[2,3-d]thiophene

The compound 2 is added to 10 ml of trifluoromethane sulfonic acid, the mixture is agitated for 24 hours, 90 ml of a solution of H$_2$O/pyridine mixed in a ratio of 8:1 solution is added thereto, and the resulting mixture is refluxed for 30 minutes. The produced solid is filtered, obtaining 0.5 g of an orange solid compound 3.

Maldi-Mass (m/z): [M]+ calcd for C$_{38}$H$_{22}$S$_2$ 542.71; found 541.73.

Manufacture of Organic Thin Film Transistor

First, a silicon wafer substrate coated with the SiO$_2$ to be 3000 Å thick is exposed to O$_2$ plasma, and then dipped in an octadecyl trichlorosilane solution diluted in hexane to a concentration of 10 mM to change the surface to be hydrophobic. Subsequently, the organic compound according to Synthesis Example 1 is vacuum-vapor deposited to be 700 Å thick by heating the substrate from room temperature to 200° C. Subsequently, source and drain electrodes are formed thereon by using a shadow mask and depositing Au to be 1000 Å thick, manufacturing an organic thin film transistor.

Evaluation

Charge mobility and current on/off ratio ($I_{on}/I_{off}$) of the organic thin film transistor according to Example 1 are calculated.

The charge mobility of the organic thin film transistor is obtained by obtaining a graph having $(I_{SD})^{1/2}$ and $V_G$ as variables from a saturation region current formula and a slope in the graph.

$$I_{SD} = \frac{WC_0}{2L} \mu (V_G - V_T)^2$$

$$\sqrt{I_{SD}} = \sqrt{\frac{\mu C_0 W}{2L}} (V_G - V_T)$$

$$\text{slope} = \sqrt{\frac{\mu C_0 W}{2L}}$$

$$\mu_{FET} = (\text{slope})^2 \frac{2L}{C_0 W}$$

In the equations, $I_{SD}$ is a source-drain current, $\mu$ or $\mu_{FET}$ is charge mobility, $C_0$ is electrostatic capacity of a gate insulating layer, W is a channel width, L is a channel length, $V_G$ is a gate voltage, and $V_T$ is a threshold voltage.

A cut-off leakage current ($I_{off}$) is a current flowing in an off state, and obtained as a minimum current in an off state. A current on-off ratio ($I_{on}/I_{off}$) is obtained as a ratio of a maximum current in an on state relative to a minimum current in the off state.

The results are shown in Table 1.

TABLE 1

| | Charge mobility (cm²/Vs) | Current on/off ratio ($I_{on}/I_{off}$) |
|---|---|---|
| Example 1 | 0.31 | 7.4 × 10⁶ |

Referring to Table 1, the organic thin film transistor according to Example 1 shows charge mobility of about 0.31 cm²/Vs and a current on/off ratio of about 7.4×10⁶, which indicate improved characteristics compared to a conventional thin film transistor.

While this disclosure has been described in connection with what is presently considered to be practical example embodiments, it is to be understood that the inventive concepts are not limited to the disclosed embodiments, but, on the contrary, is intended to cover various modifications and equivalent arrangements included within the spirit and scope of the appended claims.

What is claimed is:

1. An organic compound represented by the following Chemical Formula 1:

A-L-B [Chemical Formula 1]

wherein, in Chemical Formula 1,
L is one of a substituted or unsubstituted $C_6$ to $C_{30}$ arylene group, a substituted or unsubstituted $C_2$ to $C_{20}$ alkenylene group, a substituted or unsubstituted $C_1$ to $C_{20}$ heteroalkylene group, an oxygen atom (O), a sulfur atom (S), a selenium atom (Se), a tellurium atom (Te), and a combination thereof, and
each of an A moiety and a B moiety are independently one of the groups listed in Group 1:

[Group 1]

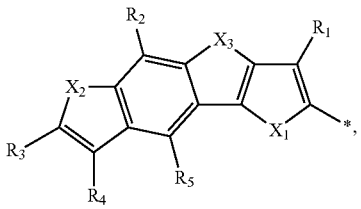

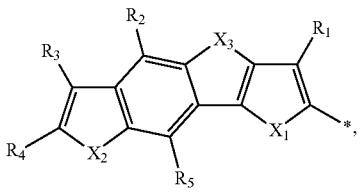

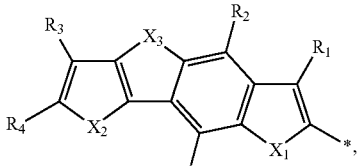

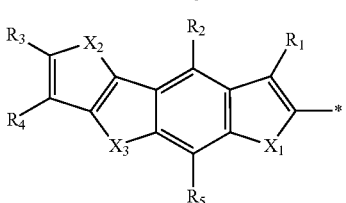

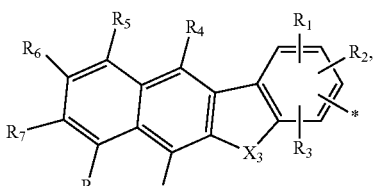

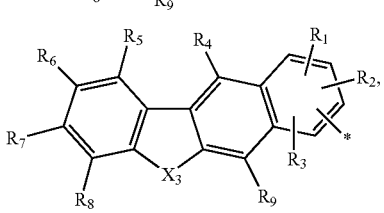

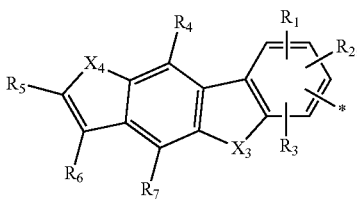

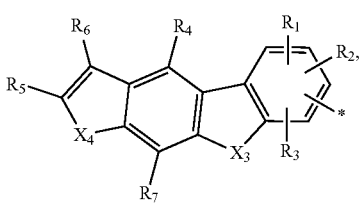

-continued

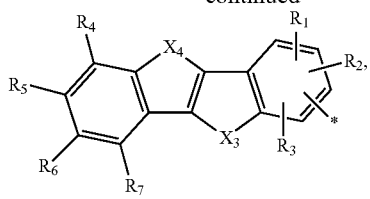

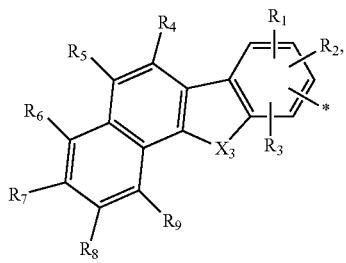

-continued

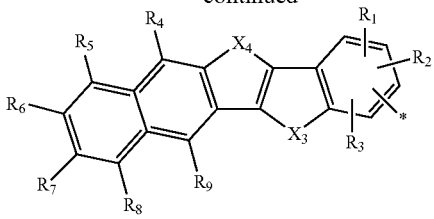

and, wherein, in the Group 1,
each of $X_1$ to $X_4$ are independently one of O, S, Se, and Te,
each of $R_1$ to $R_9$ are independently one of hydrogen, a substituted or unsubstituted $C_1$ to $C_{30}$ alkyl group, a substituted or unsubstituted $C_6$ to $C_{30}$ aryl group, a halogen atom, and a combination thereof, and
* indicates a linking point.

2. The organic compound of claim 1, wherein the organic compound is represented by one of Chemical Formulae 5 to 12, 16 to 23, and 27 to 34:

[Chemical Formula 5]

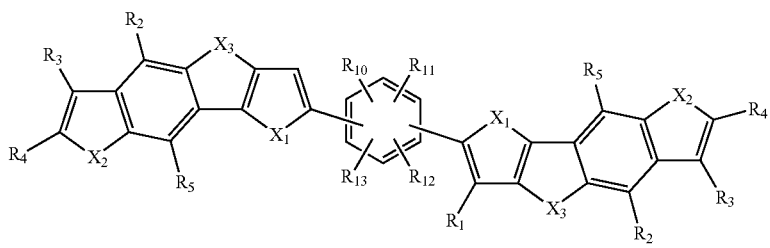

[Chemical Formula 6]

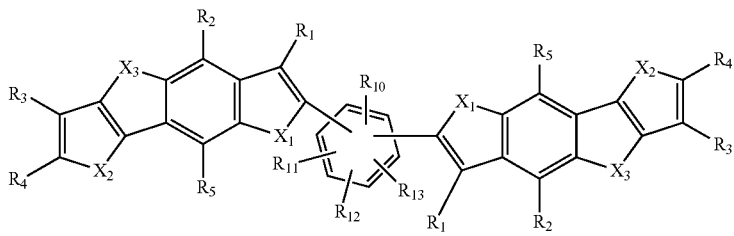

[Chemical Formula 7]

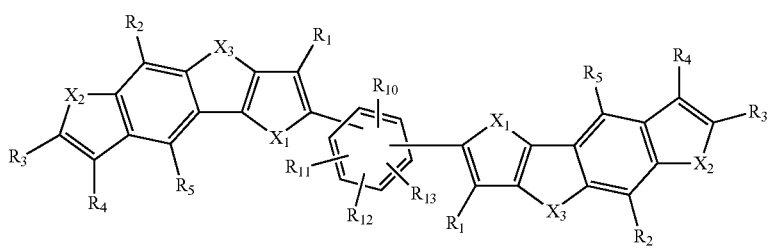

-continued
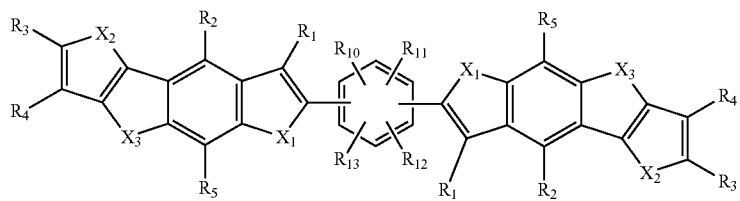
[Chemical Formula 8]
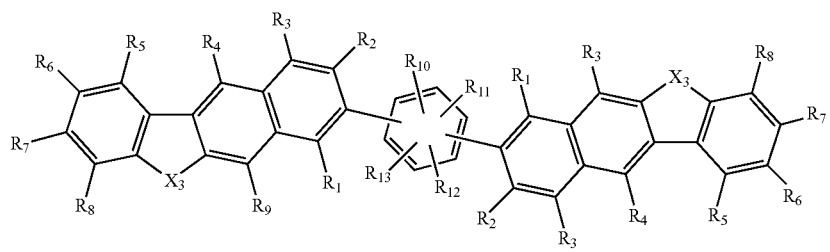
[Chemical Formula 9]
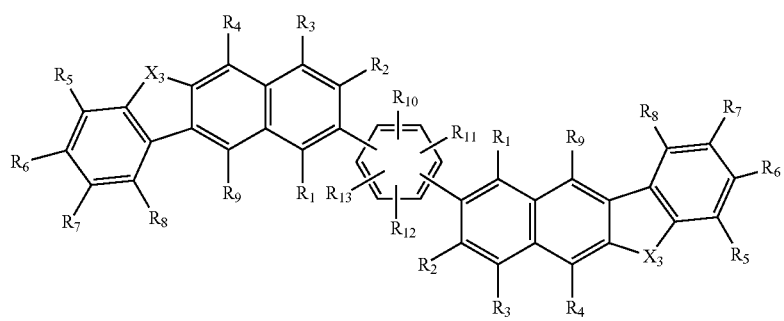
[Chemical Formula 10]
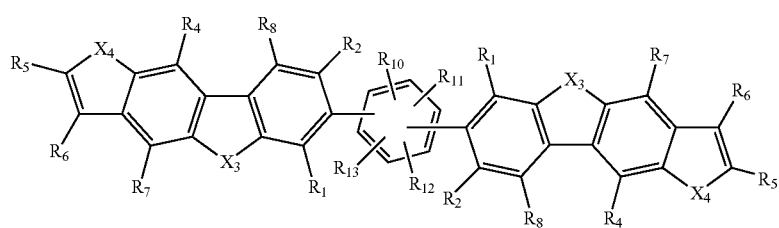
[Chemical Formula 11]
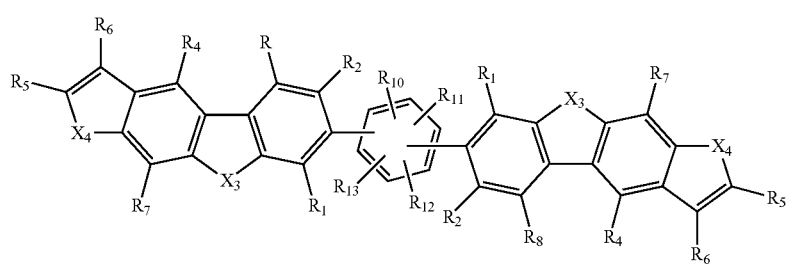
[Chemical Formula 12]
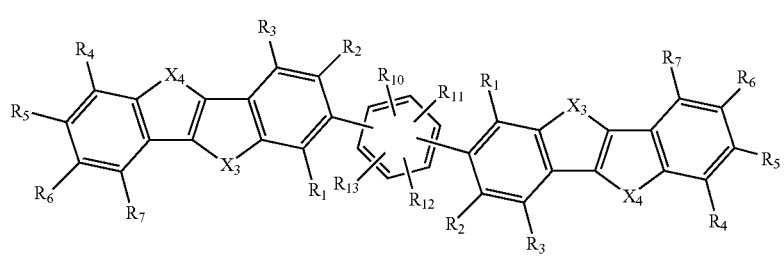
[Chemical Formula 13]

[Chemical Formula 14]
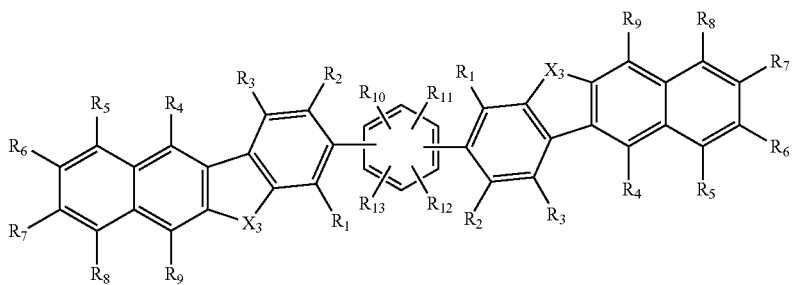
[Chemical Formula 15]
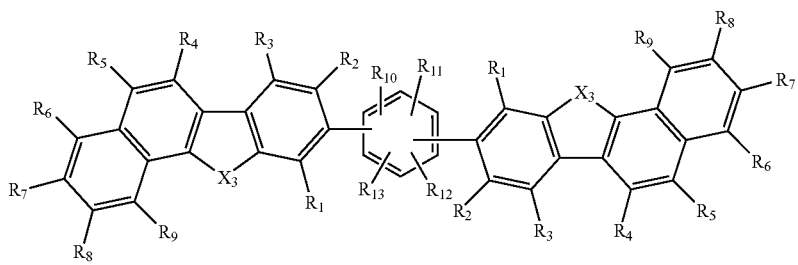
[Chemical Formula 16]
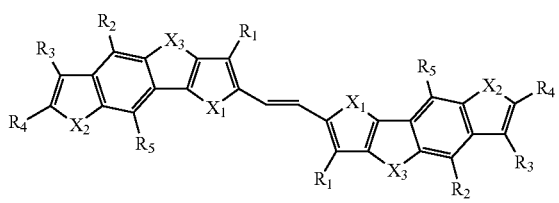
[Chemical Formula 17]
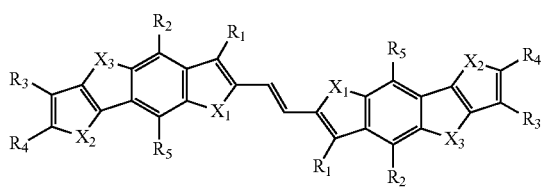
[Chemical Formula 18]
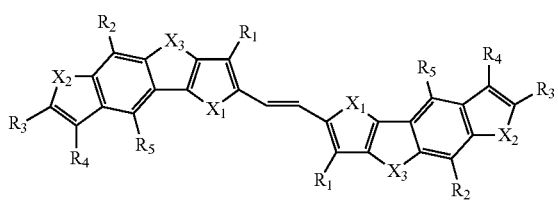
[Chemical Formula 19]
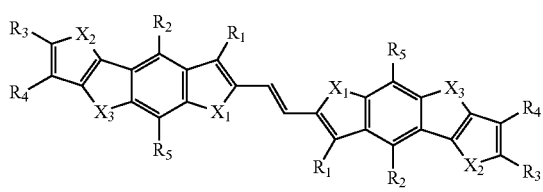
[Chemical Formula 20]
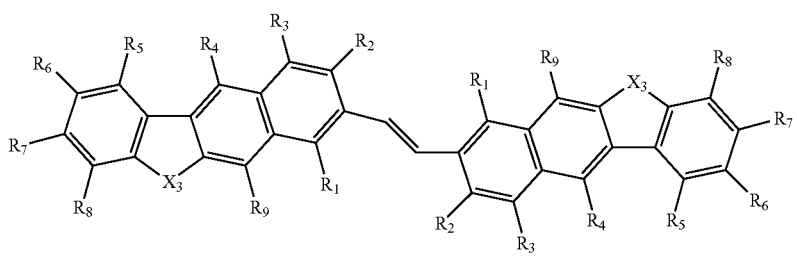
[Chemical Formula 21]
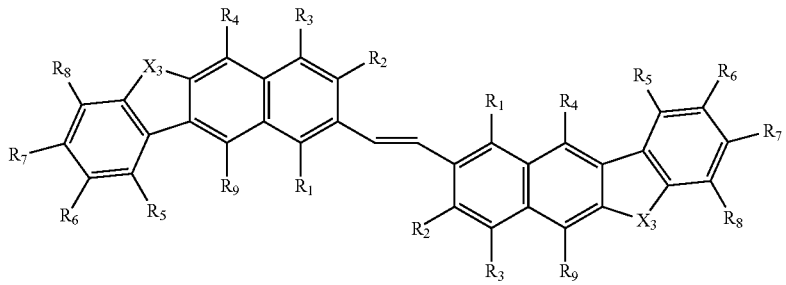

-continued
[Chemical Formula 22]
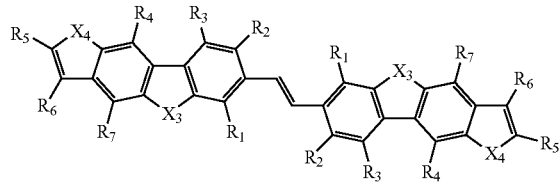
[Chemical Formula 23]
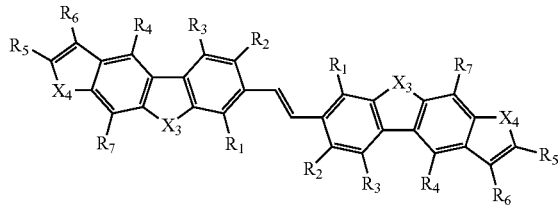
[Chemical Formula 27]
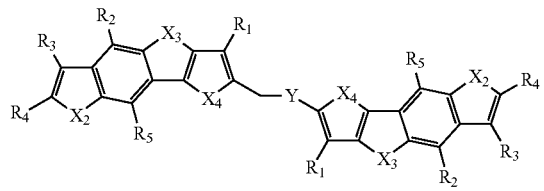
[Chemical Formula 28]
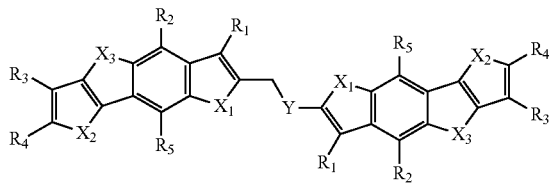
[Chemical Formula 29]
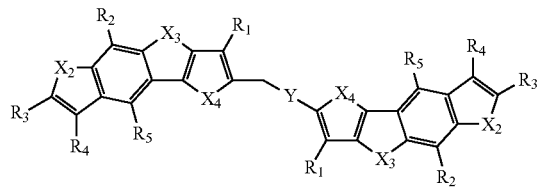
[Chemical Formula 30]
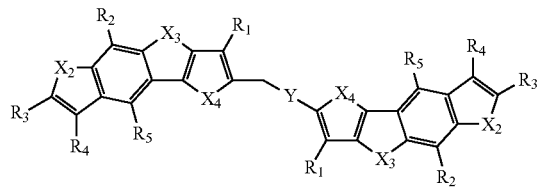
[Chemical Formula 31]
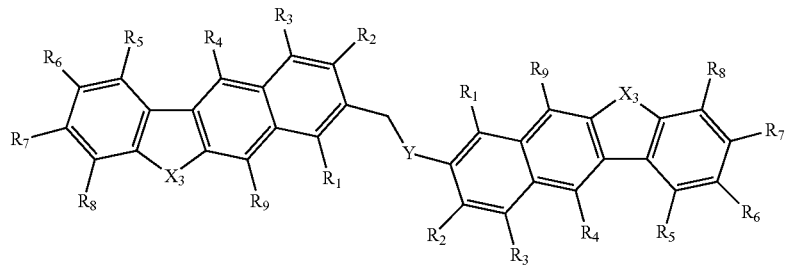
[Chemical Formula 32]
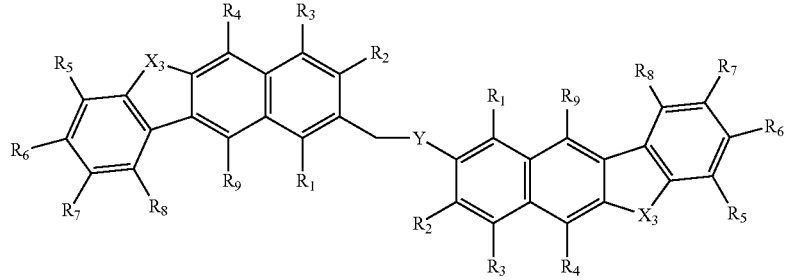
[Chemical Formula 33]
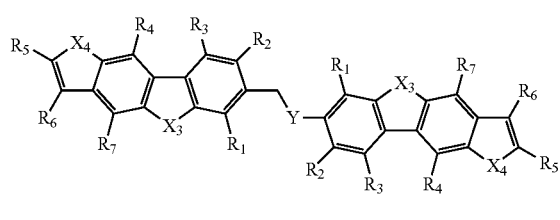
[Chemical Formula 34]

wherein, in Chemical Formulae 5 to 12, 16 to 23, and 27 to 34, each of $X_1$ to $X_4$ are independently one of O, S, Se, and Te, Y is one of O, S, Se and Te, and each of $R_1$ to $R_{13}$ are independently one of hydrogen, a substituted or unsubstituted $C_1$ to $C_{30}$ alkyl group, a substituted or unsubstituted $C_6$ to $C_{30}$ aryl group a halogen atom, and a combination thereof.

3. The organic compound of claim 2, wherein each of $R_{10}$ to $R_{13}$ of Chemical Formulae 5 to 12 are independently one of hydrogen and a halogen atom.

4. An organic thin film comprising the organic compound of claim 1.

* * * * *